United States Patent
Nag et al.

(10) Patent No.: US 11,744,834 B2
(45) Date of Patent: Sep. 5, 2023

(54) METAL-PORPHYRIN COMPLEXES FOR THE INACTIVATION OF THE BIOLOGICAL ACTIVITY OF OPIOIDS

(71) Applicant: The Government of the United States of America, as represented by the Secretary of the Navy, Arlington, VA (US)

(72) Inventors: Okhil Nag, Alexandria, VA (US); Gregory Ellis, Silver Spring, MD (US); Scott Walper, Springfield, VA (US); Jeffrey R. Deschamps, Laurel, MD (US); D. Andrew Knight, New Orleans, LA (US); James B. Delehanty, Washington, DC (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 366 days.

(21) Appl. No.: 16/837,342

(22) Filed: Apr. 1, 2020

(65) Prior Publication Data
US 2020/0316085 A1 Oct. 8, 2020

Related U.S. Application Data

(60) Provisional application No. 62/829,140, filed on Apr. 4, 2019.

(51) Int. Cl.
*A61K 31/555* (2006.01)
*A61P 25/36* (2006.01)
*A61K 47/69* (2017.01)

(52) U.S. Cl.
CPC ........ *A61K 31/555* (2013.01); *A61K 47/6929* (2017.08); *A61P 25/36* (2018.01)

(58) Field of Classification Search
CPC .............................. A61K 31/555; A61P 25/36
See application file for complete search history.

(56) References Cited

FOREIGN PATENT DOCUMENTS

JP 2009-214092 A 9/2009

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995). (Year: 1995).*
International Search Report and Written Opinion in PCT/US2020/026115 dated Jul. 16, 2020.
Grass, V. et al., "Reductive Electrochemistry of Rhodium Porphyrins. Disproportionation of Intermediary Oxidation States", Journal of the American Chemical Society, 1997, vol. 119, No. 15, pp. 3536-3542.
Fukushima, K. et al., "Synthesis and properties of Rhodium (III) porphyrin cyclic tetramer and cofacial dimer", Inorganic chemistry, 2003, vol. 42, No. 10, pp. 3187-3193.
Johnson, B. J. et al., "Porphyrin-embedded silicate materials for detection of hydrocarbon solvents", Sensors, 2011, vol. 11, No. 1, pp. 886-904.
Zhang., Y.- H. et al., "Raman and infrared spectral study of meso-sulfonatophenyl substituted porphyrins (TPPSn, n=1, 2A, 2O, 3, 4)", Spectrochimica Acta Part A: Molecular and Biomolecular Spectroscopy, 2003, vol. 59, No. 1, pp. 87-101.
Miyachi, M. et al., "Bio-inspired photoresponse of porphyrin-attached gold nanoparticles on a field-effect transistor", Biochimica et Biophysica Acta (BBA)—Bioenergetics, 2014, vol. 1837, No. 9, pp. 1567-1571.

* cited by examiner

*Primary Examiner* — Marcos L Sznaidman
(74) *Attorney, Agent, or Firm* — US Naval Research Laboratory; Roy Roberts

(57) ABSTRACT

A rhodium-loaded porphyrin complex, comprising the porphyrin (meso-tri(4-sulfonatophenyl) mono(4-carboxyphenyl)porphine (C1S3TPP)) with coordinated with rhodium, effectively neutralizes the biological activity of naturally-occurring and synthetic opioids.

2 Claims, 3 Drawing Sheets

METAL-PORPHYRIN COMPLEXES FOR THE INACTIVATION OF THE BIOLOGICAL ACTIVITY OF OPIOIDS

CROSS-REFERENCE TO RELATED APPLICATIONS

This Application claims the benefit of U.S. Provisional Patent Application No. 62/829,140 filed Apr. 4, 2019, the entirety of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 110,705.

BACKGROUND

The abuse of synthetic opioids has reached epidemic proportions on a worldwide scale, resulting in a major public health crisis [see ref. 1]. The potential weaponization of synthetic opioids on the battlefield also exists. The very real prospect of this scenario is highlighted by the 2002 incident in a Moscow theater where Russian Special Forces deployed a chemical aerosol containing a mixture of two highly potent synthetic opioid (fentanyl) derivatives: carfentanil and remifentanil against Chechen terrorists [2]. The aerosolized form of the opioids coupled with inadequate medical response resulted in 125 deaths.

Developed as a sedative for pain relief, synthetic opioids cause the depression of the respiratory system and psychomotor impairment. Acute administrations of opioids can result in overdose and death. The current state of the art for the treatment of opioid overdose is naloxone (NARCAN®), a competitive opioid receptor antagonist that has been in use since 1971. Naloxone's function is two-fold: (1) it competes with the opioid for binding to the opioid receptor and (2) it displaces opioid that is already bound to the receptor. In this capacity, naloxone decreases the activation of the intracellular opioid receptor signaling pathway while allowing the body to naturally clear the opioid through Phase I (oxidation) detoxification pathways (by cytochrome P450 enzymes in the liver). Because naloxone merely competes with and displaces bound opioid from the receptor, it often requires the administration of multiple doses until the body is able to clear the opioid from the system. In some instances, the effect of the opioid overdose cannot be overcome, even with repeated dosing. Further, because naloxone interacts directly with the opioid receptor, cessation of its usage can induce withdrawal symptoms in response to naturally-occurring opioids. Additionally, the expression of new opioid receptors as a result of habitual opioid use can render patients refractory to naloxone treatment due the overexpression of opioid receptors.

A need exists for alternative treatment for opioid overdose.

BRIEF SUMMARY

The invention described herein circumvents the aforementioned issues pertaining to the use of naloxone for the treatment of opioid overdose. The invention involves a rhodium-loaded porphyrin complex which is generated by loading the porphyrin (meso-tri(4-sulfonatophenyl) mono (4-carboxyphenyl)porphine ($C_1S_3TPP$)) with rhodium chloride trihydrate (FIG. 1).

In one embodiment, a material includes the porphyrin (meso-tri(4-sulfonatophenyl) mono(4-carboxyphenyl)porphine ($C_1S_3TPP$)) coordinated with rhodium.

In a further embodiment, a medicament includes the porphyrin (meso-tri(4-sulfonatophenyl) mono(4-carboxyphenyl)porphine ($C_1S_3TPP$)) coordinated with rhodium in conjunction with a pharmaceutically-acceptable carrier.

In yet another embodiment, a method of making the porphyrin (meso-tri(4-sulfonatophenyl) mono(4-carboxyphenyl)porphine ($C_1S_3TPP$)) with coordinated with rhodium includes contacting $C_1S_3TPP$ with a rhodium compound.

In a still further embodiment, a method of treatment includes identifying a patient known or suspected of being in a condition of opioid overdose, and providing the patient with a medicament including the porphyrin (meso-tri(4-sulfonatophenyl) mono(4-carboxyphenyl)porphine ($C_1S_3TPP$)) coordinated with rhodium.

In additional embodiments, the rhodium-coordinated porphyrin is in a state of being conjugated to the surface of a nanoparticle (such as a gold nanoparticle).

BRIEF DESCRIPTION OF THE DRAWINGS

FIG. 4A provides a MS analysis of fentanyl, morphine, and naloxone incubated with Rh-TPP, the bar graph indicating percent of remaining fentanyl, morphine, and naloxone that were incubated with Rh-TPP at a 1:1 ratio. FIG. 4B illustrates the chemical structures of fentanyl, morphine, and naloxone.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Synthetic opioids bind to the mu opioid receptor and modulate the activity of ion channels in neurons and muscle cells, resulting in sedation and analgesia (pain relief). Naloxone (NARCAN®), the current state of the art for the treatment of opioid abuse/overdose, is a competitive antagonist that binds to the opioid receptor and displaces and/or prevents binding of synthetic opioid to the receptor, thus blocking opioid activity. Two significant limitations of naloxone are: (1) the need for large repetitive doses while the body clears the opioid through natural processes, and (2) it directly ligates the opioid receptor, inducing the expression of more receptors, leading to withdrawal symptoms and decreased naloxone effectiveness.

Figure 1:
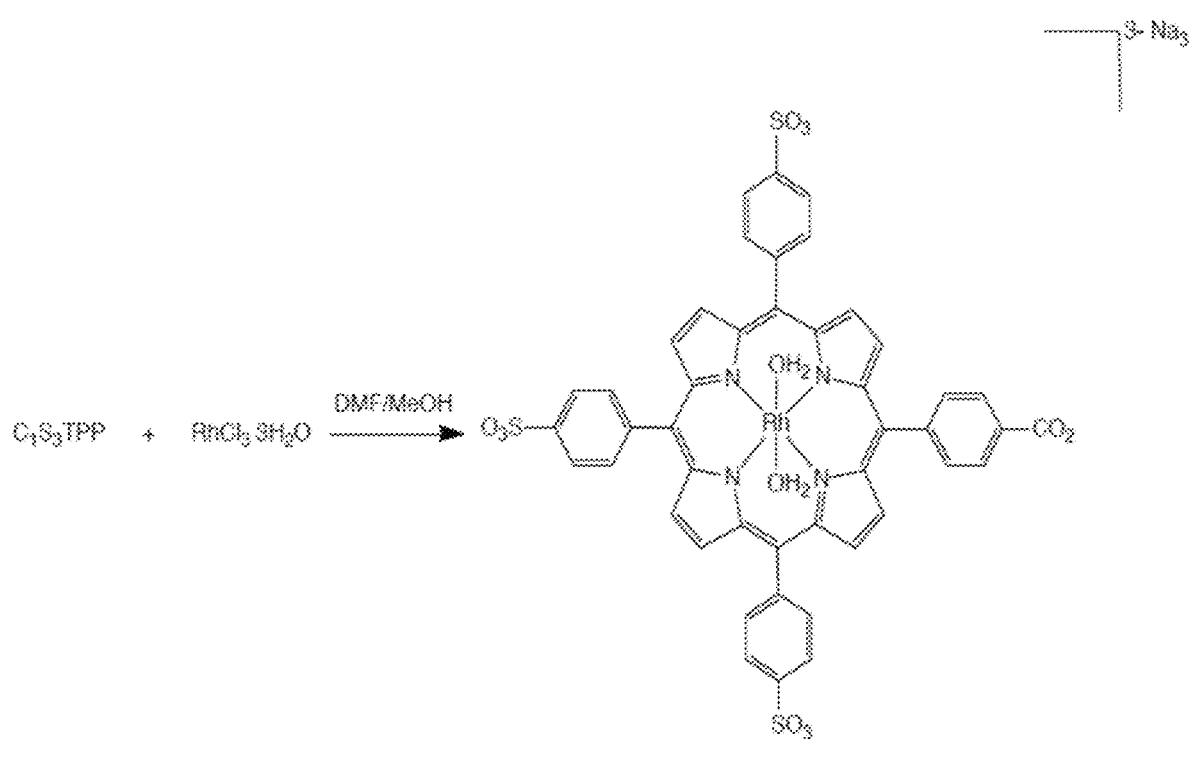
FIG. 1 illustrates formation of the rhodium-porphyrin complex (Rh-TPP) by loading the porphyrin $C_1S_3TPP$ with rhodium chloride trihydrate.

A rhodium-loaded porphyrin complex depicted in FIG. 1 (referred to herein as "rhodium complex" or "Rh-TPP complex") effectively neutralizes the biological activity of naturally-occurring and synthetic opioids. When incubated with opioids under physiological conditions, the rhodium complex effectively neutralizes opioids' ability to induce intracellular signaling pathways in cultured mammalian cells. Specifically, the complex inhibits the formation of cyclic AMP (cAMP), resulting in the deactivation of calcium and potassium ion channels.

The following were accomplished: (1) synthesis and spectroscopic characterization of the rhodium complex, (2) cytotoxicity testing of the rhodium complex in cell culture, (3) the degradation of a representative synthetic opioid (fentanyl) by the rhodium complex as characterized mass spectroscopy (MS), and (4) the functional confirmation that the rhodium complex neutralizes the opioid activity of fentanyl by more than 1,000 to 10,000 times in a tissue culture assay of opioid-induced intracellular signaling activity.

It is expected that delivery of the rhodium complex to a patient known or suspected of suffering an opioid overdose might be effective to ameliorate the effects of the overdose. Thus, a medicament is contemplated comprising the rhodium complex in conjunction with a pharmaceutically-acceptable carrier.

EXAMPLES

The Rh-TPP complex was prepared via a method previously described in the literature which involved a different porphyrin, X. Fu and B. B. Wayland, J. Am. Chem. Soc., 2004, 126, 2623, incorporated herein by reference for disclosing a technique for preparing a metal/porphyrin complex.

Figure 2:
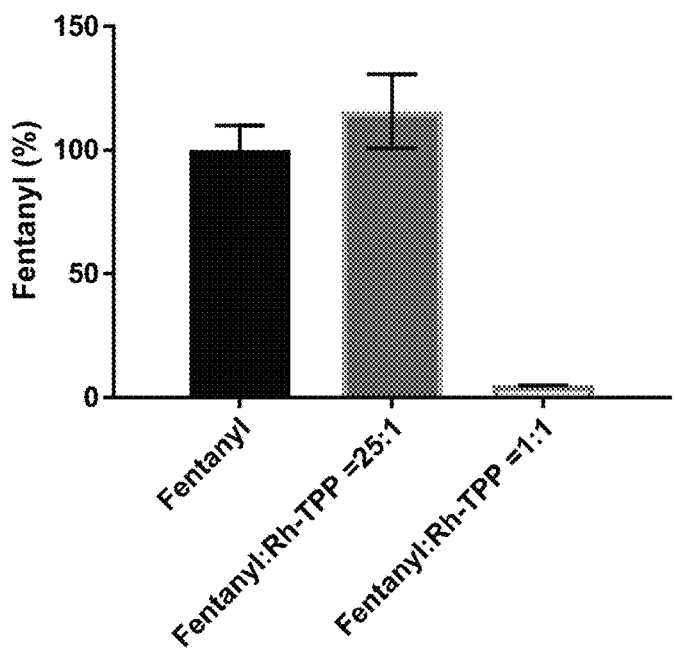
FIG. 2 provides mass spectroscopy (MS) data showing that incubation of fentanyl with Rh-TPP at a 1:1 ratio results in the disappearance of the fentanyl mass peak.
Figure 3:
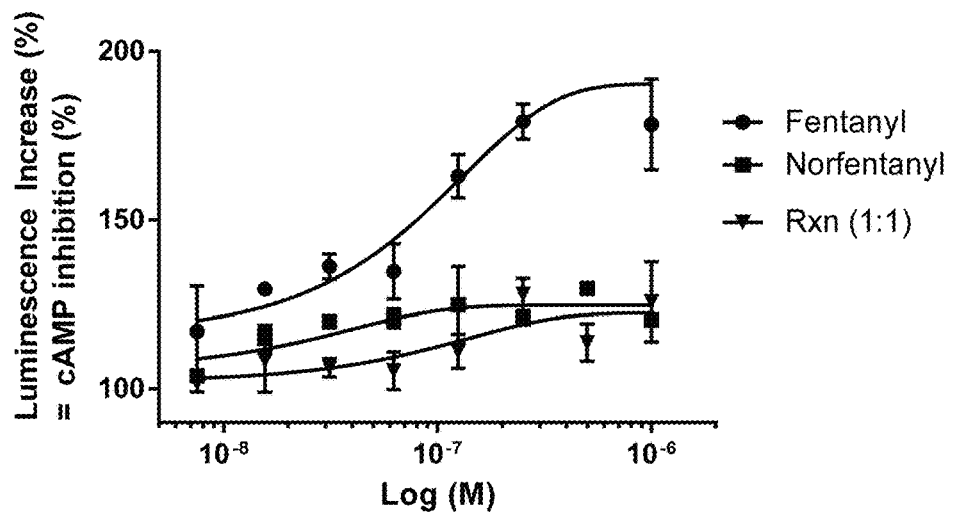
FIG. 3 shows data from assessment of the opioid activity of fentanyl after incubation with Rh-TPP complex. In a classical opioid signaling assay, fentanyl displays an IC50 of ~150 nM while the activity of norfentanyl is 3 to 4 orders of magnitude less. The opioid activity of fentanyl that was incubated with the Rh-TPP complex showed opioid activity that was comparable to norfentanyl, confirming the inhibition of opioid activity of fentanyl by the complex.

The ability of the Rh-TPP complex to neutralize opioid activity was characterized using the synthetic opioid, fentanyl, and was assessed using both mass spectroscopy (MS) (FIG. 2) and a cell-based assay for biological opioid activity (FIG. 3). FIG. 3 shows the results of MS analysis after fentanyl was incubated with the Rh-TPP complex at varying fentanyl:Rh-TPP ratios at 37° C. for 3 hours. The data show the significant disappearance of fentanyl (as tracked by quantifying the molecular weight peak of fentanyl) when it was incubated with Rh-TPP at a 1:1 ratio. These data suggest that either (1) fentanyl was cleaved or otherwise destroyed by the Rh-TPP complex in a stoichiometric/non-catalytic fashion or that (2) fentanyl was coordinated by Rh-TPP. Either scenario would result in the disappearance of the fentanyl molecular weight peak in this analysis.

Figure 4A:
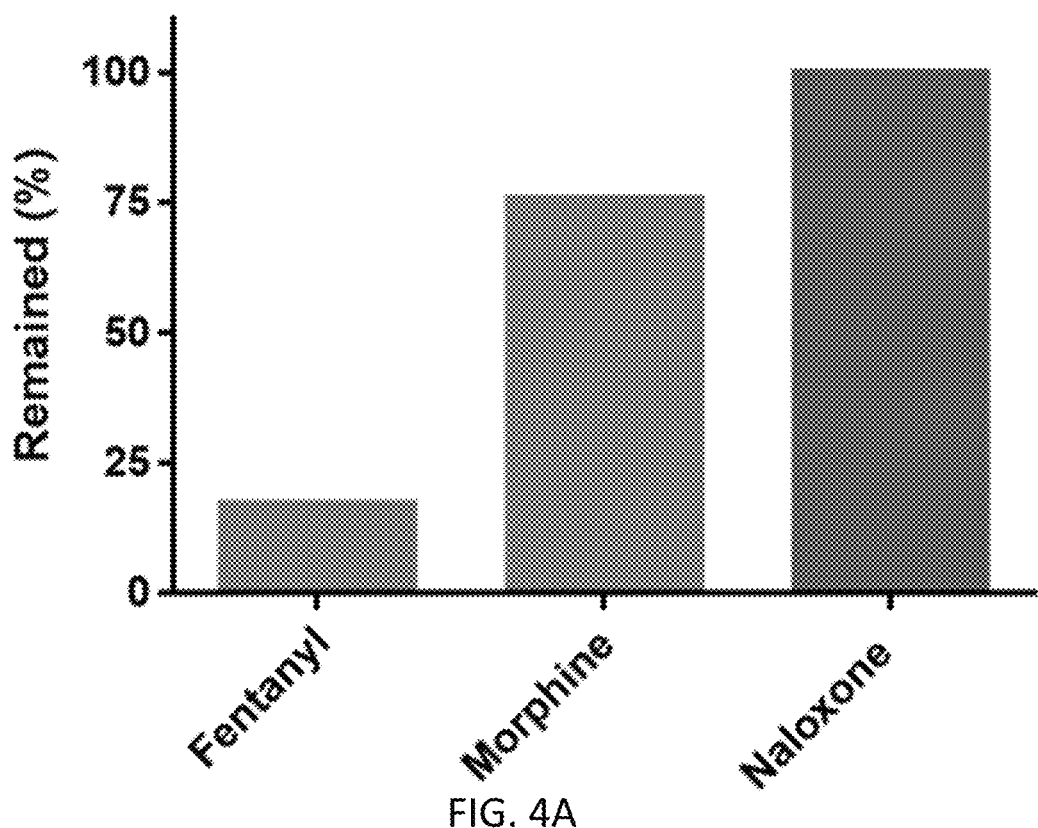
FIGS. 4A and 4B show the reactivity of Rh-TPP toward opioids and naloxone.
Figure 4B:
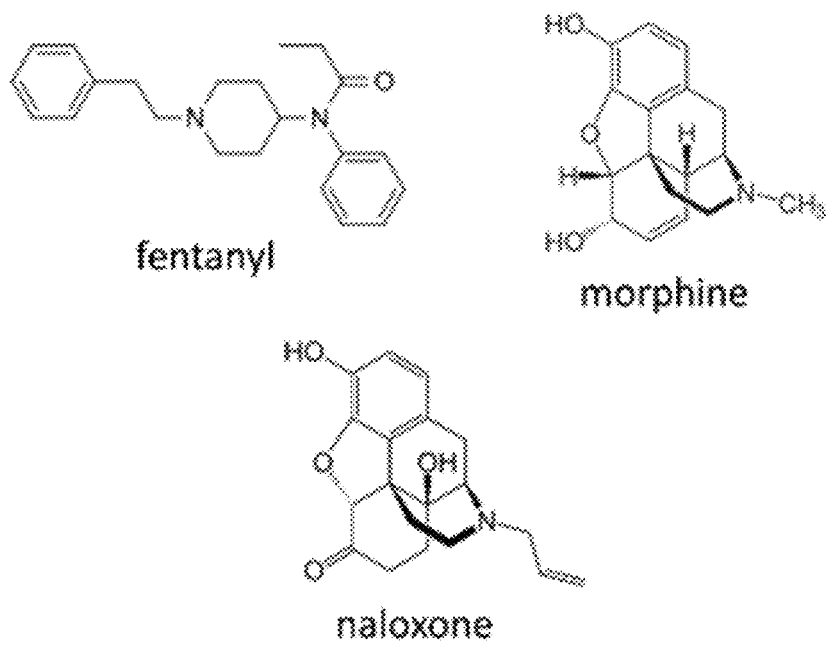

A classical cell-based opioid cellular signaling assay determined the biological activity of fentanyl after its incubation with the Rh-TPP complex, with results shown in FIG. 4. In this assay, mammalian cells were transfected to express the mu opioid receptor. The ability of fentanyl to inhibit the formation of cyclic AMP is determined by measuring the cellular levels of free ATP. Here, an increase in photoluminescence intensity quantitatively tracks active fentanyl in a dose dependent manner (circular markers). As a control, the activity of norfentanyl, known to have 1,000- to 10,000-fold less activity than fentanyl was used to confirm proper function of the assay (square markers). Notably, fentanyl incubated with the Rh-TPP complex at a 1:1 ratio showed opioid activity that was nearly identical to norfentanyl, confirming that the Rh-TPP functionally inactivated the activity of the fentanyl starting product by 1,000- to 10,000-fold (triangular markers).

The specificity/reactivity of the Rh-TPP complex was tested against fentanyl, morphine, and naloxone. FIG. 4 shows the results of MS analysis after fentanyl, morphine, or naloxone was incubated with the Rh-TPP complex at equimolecular ratio at 37° C. for 3 hours. The data show the significantly higher disappearance of fentanyl (as tracked by quantifying the molecular weight peak of fentanyl) compared with morphine, and naloxone. These data suggest that Rh-TPP is more reactive to fentanyl.

The fentanyl cleavage activity of the Rh-TPP complex was augmented by its display on the surface of inorganic nanoparticles (NPs). The Rh-TPP complex was covalently conjugated to the surface of 20 nm diameter gold NPs (~375 copies per NP). The 'turnover number' (the number of fentanyl target molecules cleaved per unit time) increased markedly when Rh-TPP was displayed in multivalent form on the AuNP surface (Table 1). Turnover numbers are calculated by dividing fentanyl consumed with Rh-TPP used.

TABLE 1

Catalytic activity of Rh-TPP conjugated to AuNP

| Fentanyl (mM) | AuNP (nM) | Rh-TPP (µM) | Fentanyl Consumed (%) | Catalytic Turnover |
|---|---|---|---|---|
| 1 | 10.0 | 3.8 | 18 | 48 |
| 1 | 5.0 | 1.9 | 16 | 85 |
| 1 | 2.5 | 0.9 | 16 | 171 |
| 1 | 1.3 | 0.5 | 15 | 320 |
| 1 | 0.6 | 0.2 | 14 | 597 |
| 1 | 10.0 | 0.0 | 0 | |
| 1 | 0.0 | 0.0 | 2 | |

Further Embodiments

It is expected that other metals besides could be used as a substitute in the porphyrin complex resulting in tailored activity.

The rhodium-porphyrin complex can be conjugated to and displayed on the surface of or in the core of various nanoparticles. Examples of these include, but are not limited to liposomes, gold nanoparticles, metal oxide particles, quantum dots, polymers, nucleic acids.

The inclusion of acid to lower the pH of the area immediately surrounding the rhodium-porphyrin complex could enhance the catalytic rate of opioid cleavage of the complex.

Other porphyrins could be used to generate the opioid-neutralizing complex.

It is expected that other forms of nanoparticle may operate similarly to the gold nanoparticles tested and found to improve activity. Accordingly, all manner of metallic, and inorganic, and organic nanoparticles are contemplated for this purpose.

Concluding Remarks

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

[1] H. Hedegaard et al. (2018) Drugs Most Frequently Involved in Drug Overdose Deaths: United States, 2011-2016. *National Vital Statistics Reports* 67: 1-13.

[2] J. R. Riches et al. (2012) Analysis of Clothing and Urine from Moscow Theatre Siege Casualties Reveals Carfentanil and Remifentanil Use *Journal of Analytical Toxicology* 36:647-656.

What is claimed is:

1. A material comprising the porphyrin (meso-tri(4-sulfonatophenyl) mono(4-carboxyphenyl)porphine ($C_1S_3TPP$)) coordinated with rhodium, wherein the porphyrin has the following structure

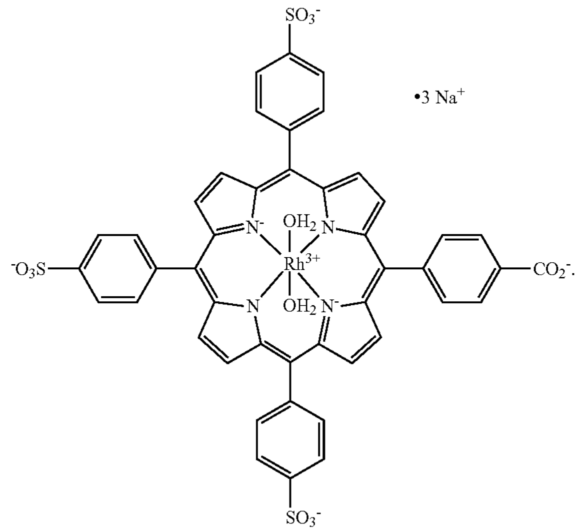

2. The material of claim 1, wherein the rhodium-coordinated porphyrin is in a state of being conjugated to the surface of a nanoparticle.

* * * * *